United States Patent [19]

Foderick

[11] 4,280,501
[45] Jul. 28, 1981

[54] INFLATABLE CATHETER MEANS AND METHOD

[76] Inventor: John W. Foderick, Box 246, Chisholm, Minn. 55719

[21] Appl. No.: 48,001

[22] Filed: Jun. 13, 1979

[51] Int. Cl.³ .......................................... A61M 25/00
[52] U.S. Cl. ................................................ 128/349 B
[58] Field of Search ............ 128/349 B, 349 BV, 348, 128/344, 246, 129

[56] References Cited

U.S. PATENT DOCUMENTS

| | | | |
|---|---|---|---|
| 3,211,151 | 10/1965 | Foderick et al. | 128/349 B |
| 3,374,509 | 3/1968 | Logan et al. | 128/348 |
| 3,516,408 | 6/1970 | Montanti | 128/349 B |
| 3,766,920 | 10/1973 | Greene | 128/349 B |
| 3,860,007 | 1/1973 | Binard et al. | 128/349 B |
| 3,889,676 | 6/1975 | Greene | 128/349 B |
| 4,198,984 | 4/1980 | Taylor | 128/349 BV |

*Primary Examiner*—Bradley Garris
*Attorney, Agent, or Firm*—Laurence R. Brown

[57] ABSTRACT

A catheter of the type having integrally attached fluid control means inflating a holding collar through a secondary inflation tube integrally attached longitudinally to the catheter is provided with a simple clamping means movable axially adjacent the catheter to pinch shut the fluid processing tube leading the collar and act as a fluid exit control valve. This permits the attached fluid control means such as a syringe to be severed with the inflation tube where it branches from the catheter and assures sterile delivery of a complete integral catheter array without the disadvantage of having to tape the syringe and/or an awkward clamp in place after positioning and inflating the collar.

9 Claims, 4 Drawing Figures

FIG. 1
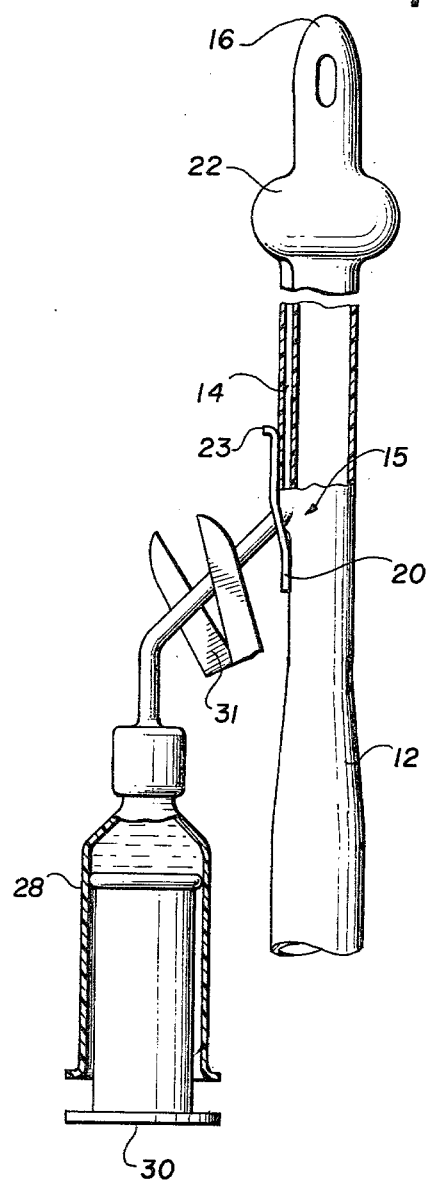
FIG. 2
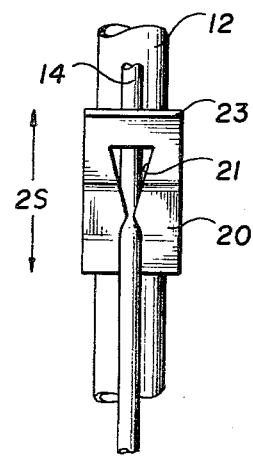
FIG. 3
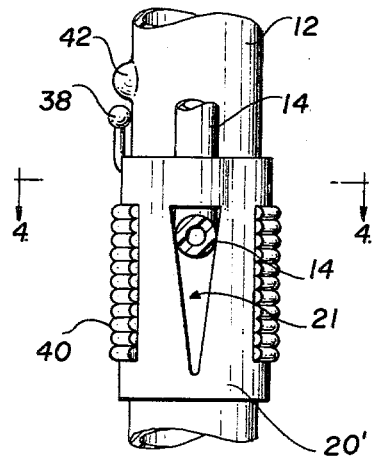
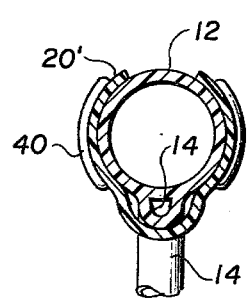
FIG. 4

INFLATABLE CATHETER MEANS AND METHOD

TECHNICAL FIELD

This invention relates to medical techniques and apparatus and more particularly it relates to catheters having inflatable collars near an innermost end for holding them in place in an orifice in the body such as the urinal tract.

BACKGROUND ART

The art of Foley type rubber catheters having an inflatable collar is well known as for example shown by U.S. Pat. No. 3,211,151 issued Oct. 12, 1965 to J. W. Foderick et al. It is usual with such catheters to have an integrally appended syringe or other inflation means for selectively transferring fluid to the collar by attachment to a secondary inflation tube carried alongside and integral with the catheter structure.

It has been usual to leave the inflation means in place after the collar is inflated. However that comprises a heavy and cumbersome appendage that can get caught on moving objects or can put weight on the catheter tending to dislodge it. Also it gets in the way during use of the catheter, which accordingly must be more carefully and delicately handled.

Various sorts of clamping structure are known for holding the fluid in the inflated collar. Typical U.S. Pat. Nos. showing clamps are 3,599,620 issued Aug. 17, 1971 to Jay Z. Balin, 3,602,226 issued Aug. 31, 1971 to Richard E. Ericson, 3,275,001 issued Sept. 27, 1966 to D. A. Rosecrans and 3,176,691 issued Apr. 6, 1965 to R. E. Ericson. All of these are subject to the problems of the foregoing paragraph.

Detachable syringes are known, mostly as used for inflation where de-inflation or venting is controlled by some kind of retaining valve structure. These U.S. Pat. Nos. are typified by 4,116,201 issued Sept. 26, 1978 to Nayan S. Shah, 3,889,676 issued June 17, 1975 to F. R. Greene, 3,905,361 issued to J. R. Hewson et al., and 3,131,694 issued May 5, 1964 to E. D. G. Garth.

All of these are subject to long tails on the inflation tube assembly and at least part of the inflation means retained thereon, which also do not overcome the foregoing problems or produce a simple inexpensive catheter arrangement that eliminates the inconvenience and possible damage to a patient.

Accordingly it is a general object of this invention to provide a simple and effective self contained sterile integral catheter device that can be used without the inconvenience and potentially dangerous presence of the inflation means after the catheter is in place with its collar inflated.

Other features, objects and advantages of the invention will be found throughout the following more detailed specification.

DISCLOSURE OF THE INVENTION

This invention relates to novel catheter construction and the method of its use in treatment of a patient. The catheter has an inflatable collar expanded by fluid transfer means coupled to a feed tube branch portion extending away from and integral with the primary catheter tubing and terminating in a syringe or other inflation means of controlling fluid for selective inflation of the collar. In accordance with this invention a simple inexpensive plastic sheetlike clamp defines a triangular aperture about the feed tube that can be moved to pinch the tube closed after the collar is inflated and which permits free passage of fluid for inflation. This then permits the feed tube and accompanying integral inflation control means to be cut off adjacent the primary catheter tube after the collar is inflated, so that no heavy, cumbersome or object catching appendages are left in place when the catheter is in use, that could injure a patient, dislodge the catheter, cause discomfort or need be treated by taping in place to avoid problems.

BRIEF DESCRIPTION OF THE DRAWINGS

FIG. 1 is a sketch, partly in section of a catheter constructed in accordance with this invention;

FIG. 2 is a partial view of FIG. 1, looking to the right;

FIG. 3 is an alternative embodiment of the invention corresponding to the view of FIG. 2; and FIG. 4 is a section view through lines 4—4 of FIG. 3.

PREFERRED MODE OF THE INVENTION

As may be seen from the drawing, a primary catheter tube 12 has integrally associated therewith in a conventional manner the inflation tube 14 terminating in the inflatable collar 22. The inflation tube branches off the catheter tube 12 at 15 and terminates in integral fluid control inflationary means such as syringe 28 controlled by plunger 30. The drawing shows fluid has expanded collar 22, which is done to hold the catheter tube 12 in place in a body after insertion into an orifice such as a urinary track.

After in place with proper fluid pressure on the collar 22, this invention provides a simplified clamping means 20, comprising simply a sheetlike plastic member defining a substantially triangular aperture 21 of appropriate larger end size to pass the inflation tube 14 for free flow of liquid therethrough and of small enough dimension at the smaller end to pinch the tube tightly and prevent fluid flow as shown in FIG. 2, for example. The tab 23 may be used for manual placement. Thus, the clamping means 20 may be moved up or down as shown by arrows 25 to clamp or unclamp the tubing 14 for control of fluid passing therethrough, and comprises an inexpensive simple plastic sheet-like member.

In accordance with this invention therefore the catheter tubing insertion end 16 is inserted into the body through a body orifice such as the urinary track (not shown) and then the collar 22 is inflated to hold it in place by means of plunger 30. This is done with the clamping means 20 positioned to permit free flow of fluid through inflation tube 14, that is with larger end of the triangular aperture encompassing the tube 14. After attaining this, the inflation tube 14 is closed to outflow of fluid by moving the clamping means 20 into the position shown in FIG. 2 to pinch the resilient rubber tubing of inflation tube 14 closed. Then the inflation means 28, 30 is severed from the branch of tube 14 close to the position 15 it branches away from the catheter as typified by cutting shears 31. Then, the inflation means need not be taped in place by the physician to avoid danger of pressure on the catheter by weight or catching some foreign object. Thus this method saves time and trouble and yet assures the sanitary deliverance of a unitary and complete catheter assembly that can be used efficiently.

The clamping means 20 surrounding the inflation tube 14 is preferably retained as close to the catheter tube 12 as possible to permit short leads when the inflation tube 14 is severed. Thus as shown by the modified clamping means 20 of FIGS. 3 and 4, it may comprise a coaxially positioned clip about catheter tube 12. This is made from sheet plastic in spring clip form that may be easily sprung over the catheter tube 12 to be put in place after threading the aperture 21 over the syringe end of the inflation tube before the syringe is affixed thereto.

Preferably the coaxial clamping means 20' has knurling 40 on its dies to permit manual positioning by sliding axially along catheter tube 12. Also preferably a simple ball 38-clip 42 detent of the type described in U.S. Pat. No. 3,211,151 is put in place with the ball on clamping means 20' and the clip structure 42 on the catheter tube 12. This permits the closed tubing occurring when the clamping means 20 is moved upwardly to pinch rubber inflation tubing 14 closed in the bottom portion of triangular aperture 21 to be locked in place so that it will not accidentally become dislodged by pressure on the inflated collar or movement of something brushing against the clamping means 20'.

For hygienic reasons the construction and use of the catheter of this invention is an important advance in the art. The use of conventional catheters has led to urinary tract infections because of their construction, which leads to bacteria entering the urinary bladder through the inserted catheter tubing. When inflating means need be connected to the catheter by a valve or such equivalent, this requires manual handling and probable unsterile contamination when attaching the inflation means. By use of a disposable sterile single use catheter of the construction afforded by this invention it is unlikely that the sterile unit will be contaminated to carry bacteria into the body cavity.

It is important therefore to prevent the unit from slipping out so that the unit will become unsterile by handling of the operator. Also it is important to have a unit that can be manipulated by a single operator such as a nurse or physician without removing both hands to connect an inflation syringe or the like, where the catheter can slip out of the bladder and require reinsertion, thereby breaking the sterile technique and causing the probability of inserting bacteria into the urinary tract.

Also the removal of the catheter is a critical operation that should be done simply without finding and fitting a syringe into a valve on the bladder inflation tube.

It is therefore evident that this invention has provided improved, useful, and novel sterile catheter structure and methods of using the catheter, whereby those features of novelty believed descriptive of the nature and spirit of the invention are defined with particularity in the claims.

INDUSTRIAL APPLICABILITY

A sterile and completely assembled catheter of the type having an inflatable collar and integral inflation means to hold the catheter in place when inserted into a body orifice has a simplified clamping structure for holding fluid in the collar after inflation while the fluid control inflation means is severed from the catheter to avoid interference or special handling by taping in place. Thus a surgeon's time may be reduced in treating a patient.

The catheter can be inserted by a single person while using one hand to hold the catheter in place while inflating and locking the inflation bladder in inflated position, and thereby avoid slippage and necessity to reinsert. It is afforded as a single use complete unit sterilized to reduce possibilities of bacterial contamination during use.

Thus, while the catheter is held in place with one hand, the other can inflate the bladder holding the tube in place and then simply slide a movable slidable plastic valve clamp with a generally triangular shaped aperture from a first position passing fluid to the inflatable bladder to a second position preventing passage of fluid to hold the bladder inflated until the catheter need be removed.

The sterile inflation means is cut off the catheter after clamping to avoid possibilities of dislodging the bladder by forces applied to the inflating means such as catching on an object when the patient is moving or because of muscular movement if it is taped to the body after insertion of the catheter. Also this provides simple removal by emptying the inflation bladder without external tools simply by manipulating the valve to reopen the inflation tube.

I claim:

1. An improved inflatable catheter structure, comprising in combination, a primary catheter tube having an insertion end and an external connector end, inflatable retention collar means near the insertion end coupled by a secondary inflation tube integral with the primary catheter tube and branching off into a resiliently deformable feed tube portion at a position near the external connector end, such feed tube portion having integrally connected to the external end thereof inflation means for selectively transferring fluid along the secondary inflation tube and into said retention collar means to inflate it, and clamping means positioned between said inflating means and the primary catheter tube adjacent said primary catheter tube having an aperture defined therein surrounding said feed tube portion which thereby retains said clamping means in a movable position to place said aperture into two opposing operational positions opening and closing said feed tube portion to the passage of fluid therethrough, thereby closing the feed tube portion when in use for severing the inflatable retention collar means from the catheter structure while retaining inflation and opening the feed tube portion for deflation after use.

2. A catheter structure as defined in claim 1 wherein the clamping means comprises a plastic platelike member defining a triangular shaped aperture movable on said feed tube portion from said opening to said closing position where the clamping means frictionally engages the feed tube portion to deform it into a position closed to passage of fluids.

3. A catheter structure as defined in claim 1 having detent structure positioned on the feed tube portion and on the clamping means for holding said clamping means in position with the liquid path through said feed tube portion closed.

4. A catheter structure as defined in claim 1 having the clamping means positioned axially alongside and adjacent the catheter tube.

5. A catheter structure as defined in claim 4 wherein the clamping means comprises a coaxially positioned clip, partially surrounding the catheter tube.

6. The method of inserting an inflatable retention catheter tube with an external catheter connector end having an appended branch inflation tube with accompanying inflation means attached to the catheter tube near the external catheter connector end into a body through a body orifice such as the urinary track, comprising the steps of inserting the catheter tube into a body orifice, inflating the catheter tube by transferring fluid through said branch tube from the inflation means to retain the catheter tube in position in a body, closing the branch inflation tube by a single movable clamp valve at a position adjacent the branch inflation tube with the catheter tube to retain the catheter tube inflated and in place in use, severing the branch tube and inflation means from the catheter tube while inflated and clamped to avoid interference with the use of the catheter tube, and opening the branch tube with said clamp valve after use to deflate the catheter tube.

7. The method of inserting an inflatable retention catheter into a body through a body orifice such as the urinary track by a single person to reduce chances of introducing infectious bacteria, comprising the steps of, inserting into a body orifice a self contained single use complete catheter unit with an appended external branch inflation tube connected to an inflatable bladder for holding the catheter in place and with accompanying means integrally attaching sterile inflation means to the branch inflation tube thereby preventing contact with the hands of an operator inserting the catheter with any part of the catheter to be inserted into the body orifice and providing all necessary structure in one integral unit including means clamping the branch inflation tube to hold bladder inflated during use thereby avoiding the necessity of diverting operator attention to affix external units to the catheter after it is inserted into a body orifice, manually retaining the location of the catheter in place in a body orifice without dislodging it while inflating the bladder with said sterile inflation means to thereby fix the catheter in place by means of said bladder, pinching closed the inflation tube to retain the bladder fully inflated with said means clamping the branch inflation tube thereby retaining the catheter in place without manual assistance of a second operator, and thereafter severing the inflation means from the branch tube with the catheter inflated to eliminate the possibility of dislodging the bladder by forces applied to the inflation means, whereby the possibilities of body track infections by bacterial contamination during placement of the catheter are decreased significantly.

8. The method defined by claim 7 including the steps of pinching the inflation tube closed by a movable valve surrounding the inflation tube comprising the means clamping the branch inflation tube and removing fluid from the inflated bladder by moving the valve to a tube opening position permitting discharge of inflation fluid through the severed branch tube after use.

9. The method of inserting a catheter tube of the inflatable retention bladder type having integral inflation means connected to a bladder by an external inflation tube into a body cavity and retaining it there comprising the steps of inserting the catheter tube into place in a cavity, inflating the bladder to hold the catheter tube in place, and moving a slidable clamp over the external inflation tube from one position passing inflation fluid through the tube to a second position retaining inflation fluid in the bladder while in use, severing the external inflation tube to remove integral inflation means with the bladder inflated, and deflating the bladder by moving the slidable clamp to a position releasing fluid from the bladder through the severed tube.

* * * * *